(12) United States Patent
Richard et al.

(10) Patent No.: US 6,174,534 B1
(45) Date of Patent: Jan. 16, 2001

(54) COSMETIC COMPOSITION AND METHOD FOR TREATING ROSACEA

(75) Inventors: Alain Richard, Saint-Nazaire; Jean Pierre Brissonnet, Vouneuil sur Vienne, both of (FR)

(73) Assignee: La Roche Posay Laboratoire, La Roche Posay (FR)

( * ) Notice: Under 35 U.S.C. 154(b), the term of this patent shall be extended for 0 days.

(21) Appl. No.: 09/243,783

(22) Filed: Feb. 3, 1999

(30) Foreign Application Priority Data

Feb. 3, 1998 (FR) .................................................. 98 01220

(51) Int. Cl.$^7$ ....................................................... A61K 7/00
(52) U.S. Cl. ............................................. 424/401; 514/938
(58) Field of Search .............................. 424/401; 514/938

(56) References Cited

U.S. PATENT DOCUMENTS

| | | |
|---|---|---|
| 4,986,982 | * 1/1991 | Scott . |
| 5,851,556 | * 12/1998 | Breton et al. . |
| 5,885,595 | 3/1999 | Corey et al. . |
| 5,976,555 | * 11/1999 | Liu et al. . |

FOREIGN PATENT DOCUMENTS

| | | |
|---|---|---|
| 0 761 204 A1 | 3/1997 | (EP) . |
| 0 755 492 A1 | 5/1997 | (EP) . |
| 2 728 165 | 6/1996 | (FR) . |

OTHER PUBLICATIONS

Revue Medicale De Liege, vol XXXIX, No. 8, Apr. 15, 1984, Approche Therapeutique De L'Acne, M. De La Brassinne, pp. 305–307.
Bordeaux Medical, vol. 16, No. 3, 1983, Traitement De L'Acne, G. Guillet et al., pp. 131–132.

* cited by examiner

*Primary Examiner*—Diana Dudash
*Assistant Examiner*—Alysia Berman
(74) *Attorney, Agent, or Firm*—Oblon, Spivak, McClelland, Maier & Neustadt, P.C.

(57) ABSTRACT

The invention relates to a composition and method for preventing and/or treating rosacea, which includes a cosmetic composition containing at least from 1 to 5% of a $C_{12}$–$C_{24}$ fatty acid, from 5 to 15% of an ester of $C_{12}$–$C_{24}$ fatty acid and of a $C_2$–$C_3$ polyalkylene oxide fragment containing from 2 to 100 polyalkylene oxide residues, from 1 to 20% of an optionally polyoxyalkylenated $C_{12}$–$C_{22}$ fatty acid glyceride containing from 0 to 20 ethylene oxide residues, from 1 to 20% of an ester of a $C_{12}$–$C_{24}$ fatty acid and of a $C_1$–$C_6$ alcohol, from 0.1 to 10% of glycerol, from 0.1 to 3% of a $C_{12}$–$C_{24}$ fatty alcohol and water, where the composition is free of metronidazole, lanthanide, tin, zinc, manganese, yttrium, cobalt, barium strontium salt, and non-photosynthetic filamentous bacteria.

14 Claims, No Drawings

COSMETIC COMPOSITION AND METHOD FOR TREATING ROSACEA

BACKGROUND OF THE INVENTION

1. Field of the Invention

The invention relates to a composition and a method for preventing and/or treating rosacea, which includes a cosmetic composition containing at least from 1 to 5% of a $C_{12}$–$C_{24}$ fatty acid, from 5 to 15% of an ester of $C_{12}$–$C_{24}$ fatty acid and of a $C_2$–$C_3$ polyalkylene oxide fragment containing from 2 to 100 polyalkylene oxide residues, from 1 to 20% of an optionally polyoxyalkylenated $C_{12}$–$C_{22}$ fatty acid glyceride containing from 0 to 20 ethylene oxide residues, from 1 to 20% of an ester of a $C_{12}$–$C_{24}$ fatty acid and of a $C_1$–$C_6$ alcohol, from 0.1 to 10% of glycerol, from 0.1 to 20% of an ester of a $C_{12}$–$C_{24}$ fatty acid and of a $C_1$–$C_6$ alcohol, from 0.1 to 10% of glycerol, from 0.1 to 3% of a $C_{12}$–$C_{24}$ fatty alcohol, this composition comprising water and not comprising any metronidazole.

2. Discussion of the Background

Rosacea, which is also referred to incorrectly as acne rosacea, is a common dermatitis mainly affecting the face in women between 30 and 50 years old, the main symptoms of which are: erythrosis of the face, couperose with telangiectasic dilatations and papulo-pustular lesions. The mechanisms giving rise to the appearance of rosacea are poorly understood, and many factors are liable to promote rosacea. For further information on this subject, reference may be made to the following articles: "Current developments in rosacea", H.N. Mouaci-Midoun, Abstract Dermato Hebdo No. 309, 27.01.1997, pp. 15–19; "Rosacée: les traitements classiques (Rosacea: Standard treatments)", J.-M. Mazer and T. Fusade, Réalités thérapeutiques en Dermato-Vénérologic, No. 52, November 1995, pp. 8–12.

French dermatologists have for many years been using, as an authoritative preparation, metronidazole in the cream Physiane® sold by the company La Roche Posay for the treatment of rosacea.

The efficacy of these preparations in treating rosacea was attributed to metronidazole (antiparasitic agent), which remains, along with the cyclines (antibiotics), one of the compounds most commonly prescribed in the treatment of rosacea, irrespective of the support in which it is incorporated.

Moreover, Physiane® was hitherto recommended as a moisturizing cream to complement standard anti-acne treatments. However, there is no link between acne and rosacea, which are two different skin complaints, and the applicant limited itself to prescribing it for its efficacy in moisturizing the skin.

In order to be effective, the current treatments for rosacea are often prescribed over long periods. However, the prolonged use of active molecules such as antibiotics is undesirable, in particular since this can induce resistance of certain bacterial strains to these molecules. In addition, the use of cyclines and of metronidazole are contra-indicated in pregnant women.

Consequently, there remains a need for a treatment for rosacea which can be used by all individuals, over a prolonged period and without any side effects.

SUMMARY OF THE INVENTION

Thus, the inventors have discovered, surprisingly, that the cream Physiane® alone, without metronidazole, is an effective equivalent to the standard treatments based on metronidazole for treating rosacea.

Accordingly, one embodiment of the invention relates to a composition for the prevention and/or treatment of rosacea, that includes at least the following constituents (i) to (vii), the percentages being given by weight relative to the total weight of the cosmetic composition:

(i) from 1 to 5% of at least one $C_{12-C24}$ fatty acid;

(ii) from 5 to 15% of at least one ester of $C_{12}$–$C_{24}$ fatty acid and of a $C_2$–$C_3$ polyalkylene oxide fragment containing from 2 to 100 alkylene oxide residues;

(iii) from 1 to 20% of at least one optionally polyoxyalkylenated $C_{12}$–$C_{22}$ fatty acid glyceride containing from 0 to 20 alkylene oxide residues;

(iv) from 1 to 20% of at least one ester of a $C_{12}$–$C_{24}$ fatty acid and of a $C_1$–$C_6$ alcohol;

(v) from 0.1 to 10% of glycerol;

(vi) from 0.1 to 3% of a $C_{12}$–$C_{24}$ fatty alcohol;

(vii) from 50 to 85% of water;

wherein the composition is free from any of metronidazole, lanthanide, tin, zinc, manganese, yttrium, cobalt, barium or strontium salt, and non-photosynthetic filamentous bacteria.

Such a composition can be applied for a prolonged period in total safety, which makes it possible to envisage using it both for treating rosacea, for which its efficacy has been illustrated below, and for preventing rosacea, by a daily use outside of the periods during which the symptoms are present.

Another embodiment of the invention is a method for treating and/or preventing rosacea, that includes applying the above composition of the invention to the skin of a person in need thereof.

Another object of the invention is a method for reducing the papulopustules due to rosacea, that includes applying the above composition of the invention to the skin of a person in need thereof.

Another object of the invention is a method for reducing the erythema associated with rosacea, that includes applying the above composition of the invention to the skin of a person in need thereof.

Another object of the invention is a method for reducing the telangiectasia associated with rosacea, that includes applying the above composition of the invention to the skin of a person in need thereof.

DESCRIPTION OF THE PREFERRED EMBODIMENTS

Various other features, objects and attendant advantages of the present invention will be more fully appreciated as the same becomes better understood from the following detailed description, which is not intended to be limiting unless otherwise specified.

Preferably, the composition of the invention satisfies at least one or more, and preferably all, of the conditions below:

the constituent (i) is a $C_{16}$–$C_{20}$ fatty acid, preferably stearic acid;

the constituent (i) is present in an amount ranging from 2 to 4%, preferably from 2.5 to 3.5%, by weight relative to the total weight of the composition;

the constituent (ii) is a $C_{16}$–$C_{20}$ fatty acid ester, preferably a stearic acid ester;

the constituent (ii) is a fatty acid ester of polyethylene oxide;

the constituent (ii) is a mixture of esters of fatty acids and of polyalkylene oxide containing, for at least one ester, from 2 to 15 alkylene oxide residues, and, for at least one ester, from 20 to 50 alkylene oxide residues;

the constituent (ii) is a mixture of fatty acid esters of polyalkylene oxide, the HLB value (defined below) of the mixture ranging from 9 to 15, preferably from 11 to 14;

the constituent (ii) is present in an amount ranging from 7 to 13%, preferably from 9 to 11%, by weight relative to the total weight of the composition;

the constituent (iii) is a mixture of at least one $C_{12}$–$C_{22}$ fatty acid glyceride and of at least one polyoxyethylenated $C_{12}$–$C_{22}$ fatty acid glyceride containing from 2 to 20 ethylene oxide residues;

the constituent (iii) is a mixture of hydrogenated palm oil and of palm kernel oil polyoxyethylenated with 4 to 10 ethylene oxide residues;

the constituent (iii) is present in amounts ranging from 1 to 10%, preferably from 2 to 5%, by weight relative to the total weight of the composition;

the constituent (iv) is a $C_{14}$–$C_{18}$ fatty acid ester, preferably a palmitic acid ester;

the constituent (iv) is a fatty acid ester of a $C_2$–$C_4$ alcohol, preferably a fatty acid ester of isopropyl alcohol;

the constituent (iv) is present in an amount ranging from 1 to 10%, preferably from 2 to 6%, by weight relative to the total weight of the composition;

the constituent (v) is present in an amount ranging from 0.5 to 5%, preferably from 0.5 to 3%, by weight relative to the total weight of the composition;

the constituent (vi) is a $C_{14}$–$C_{18}$ fatty alcohol, preferably cetyl alcohol;

the constituent (vi) is present in an amount ranging from 0.1 to 1%, preferably from 0.2 to 0.8%, by weight relative to the total weight of the composition;

the constituent (vii) is at least partly a mineral or spring water, preferably eau de la Roche Posay;

the constituent (vii) is present in an amount ranging from 65 to 80%, preferably from 70 to 80%, by weight relative to the total weight of the composition;

the constituents (iii) and (iv) represent in total at least 5% by weight relative to the total weight of the composition;

the pH of the composition is adjusted to a value ranging from 4 to 7.

The HLB (hydrophilic-lipophilic balance) of an emulsifier is calculated according to the following formula:

$$HLB = \frac{100 - L}{5}$$

in which L represents the percentage by weight of the lipophilic group relative to the weight of the entire emulsifier molecule. The HLB value of a mixture of emulsifiers is defined as the average of the HLB values of each of the emulsifiers, weighted by the amount by weight of each of the emulsifiers in the mixture.

The water used in the composition can be of any type: demineralized water, mineral water, spring water or mixtures thereof. In general, a mineral water is fit for consumption, which is not always the case for a spring water. Each of these waters contains, inter alia, dissolved minerals and trace elements. These waters are known to be used for specific treatment purposes depending on the particular trace elements and minerals they contain, such as moisturizing the skin or the treatment of certain dermatitides. The term "mineral or spring waters" will denote not only natural mineral or spring waters but also natural mineral or spring waters enriched with additional mineral and/or trace element constituents, as well as aqueous mineral and/or trace element solutions prepared from purified water (demineralized or distilled).

Preferably, the natural spring or mineral water used according to the invention can be chosen, for example, from eau de Vittel, eaux du bassin de Vichy, eau d'Uriage, eau de la Roche Posay, eau de la Bourboule, eau d'Enghien-les-Bains, eau de Saint Gervais-les-Bains, eau de Néris-les-Bains, eau d'Allevar-les-Bains, eau de Digne, eau de Maizièers, eau de Neyrae-les-Bains, eau de Lons-le-Saunier, Eaux Bonnes, eau de Rochefort, eau de Saint Christau, eau des Fumades, eau de Tercis-les-Bains and eau d'Avene.

The composition also preferably comprises at least one animal or plant protein derivative, preferably a plant protein derivative, it being possible for this derivative to be chosen from protein hydrolysates, proteins grafted at their nitrogenous end with a fatty acid, and protein hydrolysates N-acylated with a fatty acid residue. In the case of a derivative hydrolyzed from protein, the hydrolysis can be complete or partial.

The composition of the invention can be in any pharmaceutical form normally used for a topical application, in particular in the form of an oil-in-water or water-in-oil emulsion or a multiple emulsion, a dispersion of an oil in an aqueous phase using spherules, it being possible for these spherules to be polymer nanoparticles such as nanospheres and nanocapsules, or lipid vesicles of ionic and/or nonionic type.

Preferably, the composition of the invention is in the form of an oil-in-water emulsion.

Preferably, the composition of the invention satisfies all of the following conditions:

the constituent (i) is stearic acid;

the constituent (i) is present in an amount ranging from 2.5 to 3.5% by weight relative to the total weight of the composition;

the constituent (ii) is a mixture of stearic acid esters containing from 40 to 60% of at least one stearic acid ester of ethylene oxide containing from 3 to 8 ethylene oxide residues and from 40 to 60% of at least one stearic acid ester of ethylene oxide containing from 25 to 40 alkylene oxide residues;

the constituent (ii) is present in an amount ranging from 9 to 11% by weight relative to the total weight of the composition;

the constituent (iii) is a mixture of hydrogenated palm oil and palm kernel oil polyoxyethylenated with 4 to 10 ethylene oxide residues;

the constituent (iii) is present in amounts ranging from 2 to 5% by weight relative to the total weight of the composition;

the constituent (iv) is a palmitic acid ester of isopropyl alcohol;

the constituent (iv) is present in an amount of from 2 to 6% by weight relative to the total weight of the composition;

the constituent (v) is present in an amount ranging from 0.8 to 1.5% by weight relative to the total weight of the composition;

the constituent (vi) is cetyl alcohol;

the constituent (vi) is present in an amount ranging from 0.2 to 0.8% by weight relative to the total weight of the composition;

the constituent (vii) is at least partly eau de la Roche Posay;

the constituent (vii) is present in an amount ranging from 70 to 80% by weight relative to the total weight of the composition;

the constituents (iii) and (iv) represent in total at least 5% by weight relative to the total weight of the composition;

the pH of the composition is adjusted to a value ranging from 4 to 7;

the composition is in the form of an oil-in-water emulsion.

Preferably, the composition can be more or less fluid and can have the appearance of a white or coloured cream, an ointment, a milk, a lotion or a serum. It can be used as a care product and/or as a make-up product.

In a known manner, the composition of the invention can also contain the usual adjuvants in the cosmetics and dermatological fields, provided that these adjuvants do not reduce the efficacy of the composition towards rosacea. Mention may be made in particular of hydrophilic or lipophilic gelling agents, hydrophilic or lipophilic active agents, preserving agents, antioxidants, solvents, fragrances, fillers, screening agents, pigments, odour absorbers or dyestuffs. The amounts of these various adjuvants are those used conventionally in the fields considered, and, for example, from 0.01 to 20% of the total weight of the composition. Depending on their nature, these adjuvants can be introduced into the fatty phase, into the aqueous phase, into the lipid vesicles and/or into the nanoparticles.

As hydrophilic gelling agents, mention may be made in particular of carboxyvinyl polymers (carbomer), acrylic copolymers such as acrylate/alkylacrylate copolymers, polyacrylamides, polysaccharides, natural gums and clays, and, as lipophilic gelling agents, mention may be made of modified clays such as bentones, metal salts of fatty acids, hydrophobic silica and polyethylenes.

Preferable active agents which can be used in particular are vitamins, keratolytic agents and/or desquamating agents (salicylic acid and its derivatives, α-hydroxy acids, ascorbic acid and its derivatives), anti-inflammatory agents, calmants and mixtures thereof. In the event of incompatibility, these active agents can be incorporated into spherules, in particular ionic or nonionic vesicles and/or nanoparticles (nanocapsules and/or nanospheres), so as to isolate them from each other in the composition.

EXAMPLES

Having now generally described the invention, a further understanding can be obtained by reference to certain specific examples, which are provided herein for purposes of illustration only and are not intended to be limiting unless otherwise specified.

In the examples, the percentages are given by weight relative to the total weight of the composition.

Example 1

| | |
|---|---|
| Stearic acid | 3% |
| PEG-32 stearate | 5% |
| PEG-6 stearate | 5% |
| Hydrogenated palm oil/ester of palm kernel oil and of PEG-6 | 3% |
| Isopropyl palmitate | 4% |
| Glycerol | 1% |

-continued

| | |
|---|---|
| Cetyl alcohol | 0.5% |
| Anhydrous citric acid | 0.1% |
| Preserving agents | qs |
| Water | qs 100 |

An oil-in-water emulsion (Composition 1) is prepared using the constituents listed above.

Example 2 (Comparative)

| | |
|---|---|
| Stearic acid | 3% |
| PEG-32 stearate | 5% |
| PEG-6 stearate | 5% |
| Hydrogenated palm oil/ester of palm kernel oil and of PEG-6 | 3% |
| Isopropyl palmitate | 4% |
| Glycerol | 1% |
| Cetyl alcohol | 0.5% |
| Anhydrous citric acid | 0.1% |
| Metronidazole | 0.75% |
| Preserving agents | qs |
| Water | qs 100 |

Composition 2 was prepared using the constituents listed in Example 2.

In a control test, carried out under double-blind conditions on two parallel groups, 95 patients suffering from rosacea applied one or other of these creams, twice a day (morning and evening) after washing, according to a randomization (random distribution) pre-established before the start of the study. The investigator determined, on D0, D28 and D56, the number of papulo-pustules and, in parallel, the efficacy of the product. The following results were obtained:

Relative variation in the number of papulopustules between D0, D28 and D56:

| | D0–D28 D0 | D0–D56 D0 |
|---|---|---|
| Composition 1 | 26% | 41% |
| Composition 2 | 36% | 46% |

There is no significant difference between the two treatments.

Efficacy depending on the experimenter:

| | PATIENTS % | |
|---|---|---|
| | Composition 1 | Composition 2 |
| Worsened condition | 14% | 7% |
| Stable condition | 30% | 34% |
| Improved or healed rosacea | 56% | 59% |
| Reduction in the erythema | 33% | 50% |
| Reduction in the telangiectasia | 6% | 25% |

|                              | PATIENTS %    |               |
|                              | Composition 1 | Composition 2 |
|------------------------------|---------------|---------------|
| Worsened condition           | 8%            | 8%            |
| Stable condition             | 42%           | 37%           |
| Improved or healed rosacea   | 50%           | 55%           |
| Reduction in the erythema    | 29%           | 45%           |
| Reduction in the telangiectasia | 17%        | 29%           |

The differences between the cream according to the invention and the cream with metronidazole are not significant with regard to the first 3 criteria.

With regard to erythema and telangiectasia, the cream according to the invention is less effective than the cream with metronidazole, but is still significantly effective.

In addition, the same tolerance was observed (72% of good or very good tolerance) to the two creams.

This application is based on French Patent Application FR 9801220, filed Feb. 3, 1998, the entire contents of which are hereby incorporated by reference.

Having now fully described the invention, it will be apparent to one of ordinary skill that, given the teachings herein, many changes and modifications can be made thereto without departing from the spirit or scope of the invention as set forth herein.

What is claimed is:

1. A composition for treating rosacea, comprising at least the following constituents (i) to (vii), the percentages being given by weight relative to the total weight of the composition:
   (i) from 1 to 5% of at least one $C_2$–$C_{24}$ fatty acid;
   (ii) from 5 to 15% of at least one ester of a $C_{12}$–$C_{24}$ fatty acid and a $C_2$–$C_3$ polyalkylene oxide fragment containing from 2 to 100 alkylene oxide residues;
   (iii) from 1 to 20% of a mixture of hydrogenated palm oil and palm kernel oil polyoxyethylenated with 4 to 10 ethylene oxide residues;
   (iv) from 1 to 20% of at least one ester of a $C_{12}$–$C_{24}$ fatty acid and of a $C_1$–$C_6$ alcohol;
   (v) from 0.1 to 10% of glycerol;
   (vi) from 0.1 to 3% of a $C_{12}$–$C_{24}$ fatty alcohol; and
   (vii) from 50 to 85% of water;
      wherein the composition is free from any of metronidazole, lanthanide, tin, zinc, manganese, yttrium, cobalt, barium strontium salt, and non-photosynthetic filamentous bacteria.

2. The composition as claimed in claim 1, wherein
   (i) is a $C_{16}$–$C_{20}$ fatty acid present in an amount ranging from 2 to 4%, by weight relative to the total weight of the composition;
   (ii) is a $C_{16}$–$C_{20}$ fatty acid ester of polyethylene oxide; or is a mixture of esters of fatty acids and of polyalkylene oxide comprising, for at least one ester, from 2 to 15 alkylene oxide residues, and, for at least one ester, from 20 to 50 alkylene oxide residues; wherein the HLB value of the mixture (ii) ranges from 9 to 15;
   (ii) is present in an amount ranging from 7 to 13% by weight relative to the total weight of the composition;
   (iii) is a mixture of at least one $C_{12}$–$C_{22}$ fatty acid glyceride and at least one polyoxyethylenated $C_{12}$–$C_{22}$ fatty acid glyceride containing from 2 to 20 ethylene oxide residues;
   (iii) is present in an amount ranging from 1 to 10% by weight relative to the total weight of the composition;
   (iv) is a $C_{14}$–$C_{18}$ fatty acid ester of a $C_2$–$C_4$ alcohol;
   (iv) is present in an amount ranging from 1 to 10% by weight relative to the total weight of the composition;
   (v) is present in an amount ranging from 0.5 to 5% by weight relative to the total weight of the composition;
   (vi) is a $C_{14}$–$C_{18}$ fatty alcohol:
   (vi) is present in an amount ranging from 0.1 to 1% by weight relative to the total weight of the composition;
   (vii) comprises a mineral or spring water;
   (vii) is present in an amount ranging from 65 to 80% by weight relative to the total weight of the composition;
   (iii) and (iv) represent in total at least 5% by weight relative to the total weight of the composition; and
   the pH of the composition is from 4 to 7.

3. The composition as claimed in claim 1, further comprising at least one animal or plant protein derivative.

4. The composition as claimed in claim 1, wherein the composition is in the form of an oil-in-water emulsion.

5. The composition as claimed in claim 1, wherein the HLB value of (ii) is from 11 to 14.

6. The composition as claimed in claim 1, wherein (iv) is a fatty acid ester of isopropyl alcohol.

7. The composition as claimed in claim 1, wherein (v) is present in an amount of 0.5 to 3% by weight relative to the total weight composition.

8. The composition as claimed in claim 1, wherein (vi) is cetyl alcohol.

9. The composition as claimed in claim 1, wherein:
   (i) is stearic acid; and is present in an amount ranging from 2.5 to 3.5% by weight relative to the total weight of the composition;
   (ii) is a mixture of stearic acid esters containing from 40 to 60% of at least one stearic acid ester of ethylene oxide containing from 3 to 8 ethylene oxide residues and from 40 to 60% of at least one stearic acid ester of ethylene oxide containing from 25 to 40 alkylene oxide residues;
   (ii) is present in an amount ranging from 9 to 11% by weight relative to the total weight of the composition;
   (iii) is a mixture of hydrogenated palm oil and palm kernel oil polyoxyethylenated with 4 to 10 ethylene oxide residues;
   (iii) is present in amounts ranging from 2 to 5% by weight relative to the total weight of the composition;
   (iv) is a palmitic acid ester of isopropyl alcohol;
   (iv) is present in an amount of from 2 to 6% by weight relative to the total weight of the composition;
   (v) is present in an amount ranging from 0.8 to 1.5% by weight relative to the total weight of the composition;
   (vi) is cetyl alcohol;
   (vi) is present in an amount ranging from 0.2 to 0.8% by weight relative to the total weight of the composition;
   (vii) is at least partly natural spring or mineral water;
   (vii) is present in an amount ranging from 70 to 80% by weight relative to the total weight of the composition;
   (iii) and (iv) represent in total at least 5% by weight relative to the total weight of the composition;
   the pH of the composition is from 4 to 7; and
   the composition is in the form of an oil-in-water emulsion.

10. A method for treating rosacea, comprising applying the composition as claimed in claim 1 to the skin of a person in need thereof.

11. A method for reducing the papulo-pustules due to rosacea, comprising applying the composition as claimed in claim 1 to the skin of a person in need thereof.

12. A method for reducing the erythema associated with rosacea, comprising applying the composition as claimed in claim 1 to the skin of a person in need thereof.

13. A method for reducing the telangiectasia associated with rosacea, comprising applying the composition as claimed in claim 1 to the skin of a person in need thereof.

14. A method for treating rosacea, comprising applying to the skin of a person in need thereof a composition, comprising at least the following constituents (i) to (vii), the percentages being given by weight relative to the total weight of the composition:

(i) from 1 to 5% of at least one $C_{12}$–$C_{24}$ fatty acid;

(ii) from 5 to 15% of at least one ester of a $C_{12}$–$C_{24}$ fatty acid and a $C_2$–$C_3$ polyalkylene oxide fragment containing from 2 to 100 alkylene oxide residues;

(iii) from 1 to 20% of a mixture of hydrogenated palm oil and palm kernel oil polyoxyethylenated with 4 to 10 ethylene oxide residues;

(iv) from 1 to 20% of at least one ester of a $C_{12}$–$C_{24}$ fatty acid and of a $C_1$–$C_6$ alcohol;

(v) from 0.1 to 10% of glycerol;

(vi) from 0.1 to 3% of a $C_{12}$–$C_{24}$ fatty alcohol; and (vii) from 50 to 85% of water;

wherein the composition is free from any of metronidazole, lanthanide, tin, zinc, manganese, yttrium, cobalt, barium or strontium salt, and non-photosynthetic filamentous bacteria.

* * * * *

UNITED STATES PATENT AND TRADEMARK OFFICE
CERTIFICATE OF CORRECTION

PATENT NO. : 6,174,534 B1
DATED : January 16, 2001
INVENTOR(S) : Alain Richard et al.

Page 1 of 1

It is certified that error appears in the above-identified patent and that said Letters Patent is hereby corrected as shown below:

Column 7,
Line 33, "$C_2$-$C_{24}$" should read -- $C_{12}$-$C_{24}$ --;
Line 47, "barium strontium" should read -- barium salt strontium --.

Signed and Sealed this

Twenty-fifth Day of September, 2001

Attest:

*Nicholas P. Godici*

NICHOLAS P. GODICI
*Attesting Officer*  *Acting Director of the United States Patent and Trademark Office*